United States Patent [19]

Philippe

[11] Patent Number: 5,550,225
[45] Date of Patent: Aug. 27, 1996

[54] PROCESS FOR PREPARING MONOESTERS PREDOMINANTLY IN THE 6 POSITION OF D-MALTOSE, THEIR USE IN COSMETIC, BUCCAL-DENTAL, PHARMACEUTICAL AND FOOD COMPOSITIONS

[75] Inventor: Michel Philippe, Antony, France

[73] Assignee: L'Oreal, Paris, France

[21] Appl. No.: 37,172

[22] Filed: Mar. 26, 1993

[30] Foreign Application Priority Data

Mar. 30, 1992 [FR] France ................................ 92 03812

[51] Int. Cl.$^6$ .............. C07H 1/00; C07H 13/04; A61K 31/715; C13K 7/00
[52] U.S. Cl. .................. 536/115; 536/116; 536/119; 536/124; 514/53
[58] Field of Search ................ 536/119, 124, 536/115, 116; 514/53

[56] References Cited

U.S. PATENT DOCUMENTS

| | | | |
|---|---|---|---|
| H937 | 7/1991 | Sloan | 426/549 |
| 4,058,537 | 11/1977 | Mueller | 549/242 |
| 4,499,020 | 2/1985 | Lalezari | 536/28.55 |

FOREIGN PATENT DOCUMENTS 9101322  2/1991  WIPO .

OTHER PUBLICATIONS

Nishikawa et al, "Chemical and Biochemical Studies on Carbohydrate Esters, IV. Antitumor Effect of Selectively Fatty Acylated Products of Maltose", Chemical and Pharmaceutical Bulletin, vol. 29, No. 2, 1981, pp. 505–513.

*Primary Examiner*—John Kight
*Assistant Examiner*—Everett White
*Attorney, Agent, or Firm*—Cushman Darby & Cushman, L.L.P.

[57] ABSTRACT

A process for preparing monoesters predominantly in the 6' position of D-maltose involves, in a first step forming in an organic solvent a mixed anhydride of formula (I):

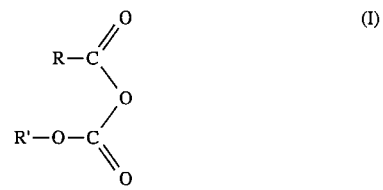

wherein R represents a linear or branched alkyl or alkenyl radical having 7–21 carbon atoms or R represents a defined mixture of the alkyl or alkenyl radicals, and R' represents a linear or branched alkyl having 2–10 carbon atoms, by reacting in the presence of a base, an R—COOH acid wherein R has the meaning given above with a ClCOOR' alkyl chloroformate wherein R' has the meaning given above, and in a second step reacting the mixed anhydride of formula (I) in solution in an organic solvent with D-maltose. The monoesters are employed in cosmetic, buccal-dental, pharmaceutical or food compositions.

14 Claims, No Drawings

PROCESS FOR PREPARING MONOESTERS PREDOMINANTLY IN THE 6 POSITION OF D-MALTOSE, THEIR USE IN COSMETIC, BUCCAL-DENTAL, PHARMACEUTICAL AND FOOD COMPOSITIONS

The present invention relates to a new process for the preparation of monoesters predominantly in the 6' position of D-maltose and to their use in various industrial fields, such as the cosmetic, buccal-dental, pharmaceutical and food industries.

Various syntheses of polyols, in particular disaccharides, have been proposed but none of these syntheses describes the preparation of monoesters predominantly in the 6' position of D-maltose.

Among recent processes for the preparation of polyol esters, mention can principally be made of the process described in patent application WO 91/01322. This process involves, in a first step, the preparation, in an aqueous medium, of a mixed carboxylic-carbonic acid anhydride to be esterified and in a second step, reacting the said mixed anhydride with a polyol.

However, this synthesis method, in an aqueous medium, does not produce monoesters in the 6' position of the D-maltose.

After various studies, the applicant has now observed, in an unexpected manner, that it is possible to obtain, primarily, monoesters in the 6' position of D-maltose by employing a method using a mixed carboxylic-carbonic anhydride but effecting the synthesis in an organic solvent medium. This is in sharp contrast to the method according to patent application WO 91/01322, as indicated above, where the synthesis is effected in an aqueous medium, preferably in water.

The present invention thus relates to a process for preparing monoesters predominantly in the 6' position of D-maltose, said process comprising, in a first step, forming in an organic solvent, a mixed anhydride of formula (I):

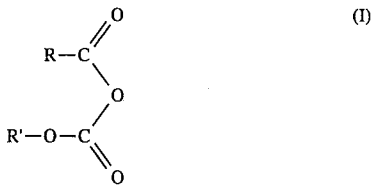

wherein

R represents linear or branched alkyl or alkenyl, having 7–21 carbon atoms or R represents a defined mixture of such alkyl or alkenyl radicals, and R' represents a linear or branched alkyl having 2 to 10 carbon atoms, by reacting, in the presence of a base, an R—COOH acid wherein R has the same meaning given above, and a ClCOOR' alkyl chloroformate wherein R' has the same meaning given above, and in a second step, reacting the said mixed anhydride of formula (I) in solution in an organic solvent with D-maltose.

As the organic solvent employed in the reaction, there can be employed, in accordance with the invention, tetrahydrofuran, N,N-dimethylformamide or N-methyl pyrrolidone.

The base, serving to activate the acid, is preferably an organic base selected from among triethylamine, pyridine, 4-dimethylaminopyridine, tributylamine or even N-methylmorpholine.

The second step, or the esterification step, of the present invention can optionally be effected after filtering the salts formed during the first stage and the D-maltose is preferably in solution in pyridine, or optionally in dimethylformamide, N-methylpyrrolidone or dimethylacetamide.

In accordance with the invention at least three equivalents of D-maltose are employed relative to the acid reacted in the first step.

According to the invention, the alkyl chloroformate is preferably selected from among ethyl chloroformate and isopropyl chloroformate.

At the end of the reaction, the solvents are evaporated and the resulting product can be chromatographed on a silica gel column using, preferably, a solvent mixture based on methylene chloride and methanol.

The reaction temperature of the process is generally between −25° and +40° C. and the reaction time between 3 and 15 hours.

The R—COOH acid is preferably selected from among octanoic acid, dodecanoic acid, tetradecanoic acid, hexadecanoic acid and oleic acid.

The monoesters predominantly in the 6' position of D-maltose, obtained by the process according to the invention as described above, can be represented by the following general formula:

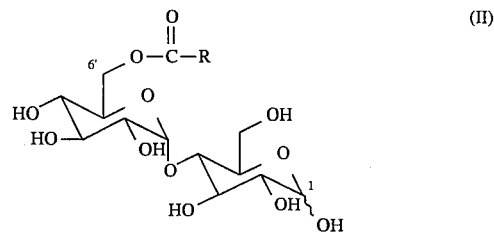

wherein

R represents linear or branched alkyl or alkenyl, having 7–21 carbon atoms or R represents a defined mixture of such alkyl or alkenyl radicals, the monoester in the 6' position representing at least about 70 percent by weight, the remainder being constituted essentially by a monoester in the 1 position.

Among the monoesters primarily in the 6' position of D-maltose of formula (II), in accordance with the invention, mention can principally be made of the following:

6'-O-octanoyl-D-maltose,
6'-hexdecanoyl-D-maltose,
6'-O-oleoyl-D-maltose,
6'-O-dodecanoyl-D-maltose and
6'-O-tetradecanoyl-D-maltose.

The determination of the structures of the products obtained has been effected by NMR$^{13}$C and $^1$H (250 Mhz in deuterated dimethyl sulfoxide (DSMO)).

The process of the invention, relative to known processes, leads to monoesters of D-maltose, perfectly defined as to their structure and composition, which is a major advantage with respect to known maltose esters which, most often, are mixtures of mono- and polyesters.

This is altogether of prime importance with respect to the value and use of these compounds, principally in the cosmetic, pharmaceutical, buccal-dental and food industries.

In effect, because of the good characterization of the monoesters, better control of the efficacy and harmlessness of compositions containing them can be achieved.

The monoesters of D-maltose of formula (II), such as defined above, exhibit relative to known esters, some very interesting properties and can principally be employed in the cosmetic, pharmaceutical and food fields.

Among these properties, mention can particularly be made of their ability to lower surface tension which is not modified even in the presence of saline solutions (0.1M NaCl and 0.033M $CaCl_2$). Moreover, the monoesters of D-maltose of formula (II), principally when R represents an alkyl radical having 13–21 carbon atoms, can form vesicles in combination with cholesterol and sodium dicetylphosphate, for example, in the respective amounts of 47.5/47.5/5 or 62.5/32.5/5. In the hydrated state, these combinations in effect, produce lamellar phases Lα starting from ambient temperature, these lamellar phases being dispersible in the form of vesicles.

The monoesters of D-maltose of formula (II) also exhibit a weak hemolytic power, principally with respect to corresponding glucose derivatives. Moreover, they exhibit a cytotoxicity clearly very inferior to that of analogous glucose derivatives, principally to those having an oleic chain.

It is appropriate, finally, to underline that the monoesters of D-maltose of formula (II) are entirely biodegradable and less ecotoxic than commercial glucose derivatives, all while exhibiting good chemical stability.

Thus, the present invention also relates to the use of monoesters of D-maltose of formula (II) as detergent agents, foaming agents, emulsifying agents, agents contributing to hydration of the skin and substances capable of forming vesicles. In cosmetic compositions, the monoesters of D-maltose are particularly useful as mild detergents for the skin and hair.

The present invention also relates to a cosmetic, buccal-dental, pharmaceutical or food composition comprising in an appropriate vehicle, at least one monoester of D-maltose of formula (II) as defined above.

In the compositions, according to the invention, the monoester of D-maltose is generally present in an amount ranging from 0.01 to 30 percent, but preferably from 0.5 to 15 percent, by weight based on the total weight of the composition.

The compositions according to the invention can be provided under various forms, principally in the form of lotions, foams or non-foams, emulsions having a liquid or semi-liquid consistency, such as milks obtained by dispersion of an oily phase in an aqueous phase, or inversely, suspensions or emulsions having the soft consistency of a cream or pomade, gels or even solid preparations such as sticks, cleansing bars, impregnated pads or even in the form of hydrating masks.

As a vehicle for the compositions according to the invention, there can be employed water, organic solvents compatible with topical application, such as acetone, isopropyl alcohol, ethyl alcohol, triglycerides of $C_6$–$C_{24}$ fatty acids, glycol ethers, such as lower alkyl ethers of mono-or dialkylene glycol, the alkylene radical of which has from 2 to 4 carbon atoms.

Also usefully employed as the solvent are esters of polyalkylene glycol and a short chain $C_1$–$C_4$ acid or even volatile silicones.

The compositions according to the invention can also contain fatty bodies such as natural or synthetic oils.

The compositions in accordance with the invention can also contain thickening or gelling agents, such as cellulose or cellulose derivatives. The thickening agents can also be acrylic polymers, alginates, gums such as xanthan, guar or carob gum or gum arabic or even polyethylene glycols, bentonites and montmorillonites.

The composition according to the invention can also contain active materials such as hydrating agents, as well as adjuvants such as antioxidants, preservatives, perfumes and dyes.

The compositions in accordance with the invention can also be provided in the form of solutions or dispersions containing the monoesters of D-maltose in vesicular form, the vesicle thus being able to serve as encapsulation agents for lipophilic and/or hydrophilic active ingredients.

General Process for Preparing
6'-O-Alkanoyl-D-Maltoses

The carboxylic acid, R—COOH, is dissolved in an organic solvent, such as 25% tetrahydrofuran (w/v). To this solution 1.05 equivalents of triethylamine are added and the medium is stirred at ambient temperature for 1 hour. The solution of the resulting triethylamine salt is then added to a solution of an alkyl chloroformate, ClCOOR', preferably, isopropyl chloroformate (1 eq.) in tetrahydrofuran (10% w/v) cooled to −20° C. with an alcohol/solid carbon dioxide bath. After the addition, the medium is left with stirring for a minimum of 3 hours.

D-maltose (≅3 eq.), in a parallel manner, is dissolved in a basic solvent such as anhydrous pyridine (7 ml/g) and the preceding medium, optionally filtered, is added to the D-maltose solution at ambient temperature for at least 3 hours.

After evaporation of the solvents, the product is chromatographed on a silica gel column by using a mixture of solvents based on methylene chloride and methanol.

Purification by chromatography can optionally be substituted by liquid/liquid extraction.

In accordance with this general process the following 6'-O-alkanoyl-D-maltoses have been prepared.

EXAMPLE 1

6'-O-octanoyl-D-maltose

Yield=35%

Melting point=98° C.

| Elemental analysis: $C_{20}H_{36}O_{12} \cdot 0.5H_2O$; MW = 477.5 | | |
|---|---|---|
|  | C % | H % |
| Calculated | 50.30 | 7.81 |
| Found | 50.07 | 7.62 |

The $NMR^{13}C$ (DSMO $D_6$) conforms to the expected structure.

EXAMPLE 2

6'-O-hexadecanoyl-D-maltose

Yield=40%

Melting point=95° C.

| Elemental analysis: $C_{28}H_{52}O_{12} \cdot 0.5H_2O$; MW = 589.7 | | |
|---|---|---|
|  | C % | H % |
| Calculated | 57.03 | 9.05 |
| Found | 56.62 | 8.64 |

The $NMR^{13}C$ (DSMO $D_6$) conforms to the expected structure.

EXAMPLE 3

6'-O-oleoyl-D-maltose

Yield=50%
Melting point=82° C.

Elemental analysis: $C_{30}H_{54}O_{12} \cdot 1.5H_2O$; MW = 633.8

|  | C % | H % |
|---|---|---|
| Calculated | 56.85 | 9.06 |
| Found | 56.55 | 8.78 |

The NMR$^{13}$C (DSMO D$_6$) conforms to the expected structure.

EXAMPLE 4

6'-O-dodecanoyl-D-maltose

Yield=40%
Melting point=93° C.

Elemental analysis: $C_{24}H_{44}O_{12} \cdot 0.5H_2O$; MW = 533.6

|  | C % | H % |
|---|---|---|
| Calculated | 54.02 | 8.50 |
| Found | 54.06 | 8.39 |

NMR$^{13}$C and $^1$H spectrum (250 Mhz in DMSO + D6 + D$_2$O)

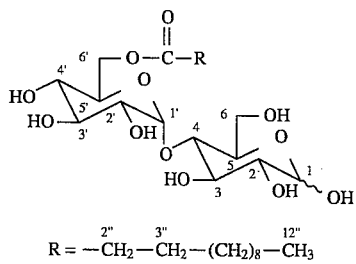

$R = -CH_2-CH_2-(CH_2)_8-CH_3$

| $^1$H peaks (ppm) | | | $^{13}$C peaks (ppm) | |
|---|---|---|---|---|
| 0.85 | triplet | H12" | 13.98 | C12" |
| 1.23 | multiplet | (CH$_2$)$_8$ | 22.12 | C11" |
| 1.50 | multiplet | H3" | 24.14 to 24.51 | C3" |
| 2.30 | triplet | H2" | 28.40 to 29.03 | (CH$_2$)$_6$ |
| 2.94 to 3.62 | multiplets | H2 to H6- H2' to H5' | 31.31 | C10" |
| 4.02 | multiplet | H6' | 39.34 - 33.38 | C2" |
| 4.26 | multiplet | H6' | 60.11 to 60.77 | C6 and C6' nonsubstituted |
| 4.38 | H1β | | 63.55 | C6' substituted |
| 4.54 | OH | | 70.00 to 81.12 | C2' to C5' and C2 to C5 |
| 4.90 to 5.00 | multiplet | H1'-H1'α | 92.08 | C1α |
| 5.53 | OH | | 96.79 | C1β |
| | | | 100.81 | C1' |
| | | | 172.95 | C1" Supplementary Peak |
| | | | 93.94 | C1β maltose substituted at 1 (23%) |

EXAMPLE 5

6'-O-tetradecanoyl-D-maltose

Yield=55%
Melting Point=110° C.

Elemental Analysis: $C_{26}H_{48}O_{12} \cdot 0.5H_2O$; MW = 561.3

|  | C % | H % |
|---|---|---|
| Calculated | 55.6 | 8.79 |
| Found | 55.44 | 8.84 |

The NMR$^{13}$C (DSMO D$_6$) conforms to the expected structure.

Examples of Cosmetic Compositions

EXAMPLE 6

Vesicular Composition in the Form of a Thick Cream

Initially a lipidic phase is prepared by mixing the following ingredients:

| | |
|---|---|
| 6'-O—hexadecanoyl-D-maltose obtained in Example 2, above | 47.53 g |
| Cholesterol | 47.53 g |
| Sodium dicetylphosphate | 4.94 g |

This lipidic phase, in an amount of 3 to 10 percent by weight, is then employed for the preparation of the vesicular composition in accordance with known procedures, the remainder of the composition being constituted by water to which optionally are added preservatives and/or antioxidants and optionally an oil.

EXAMPLE 7

Vesicular Composition in the Form of a Fluid Cream

Initially a lipidic phase is prepared by mixing the following ingredients:

| | |
|---|---|
| 6'-O—tetradecanoyl-D-maltose, obtained in Example 5, above | 62.53 g |
| Cholesterol | 32.53 g |
| Sodium dicetylphosphate | 4.94 g |

This lipidic phase, in an amount ranging from 3 to 10 percent by weight, is then employed for the preparation of the vesicular composition in accordance with known procedures, the remainder of the composition being constituted by water to which optionally are added preservatives and/or antioxidants and optionally an oil.

EXAMPLE 8

Foaming Composition

| | |
|---|---|
| 6'-O—dodecanoyl-D-maltose, obtained in Example 4, above | 5 g |
| Triethanolamine lauryl sulfate, 40% in water | 40 g |

-continued

| | |
|---|---|
| Cocoyl betaine | 4 g |
| Diethanolamide of copra acids | 3 g |
| Preservatives | 0.2 g |
| Water, sufficient amount for | 100 g |

EXAMPLE 9

Composition in the Form of an Emulsion

| | |
|---|---|
| 6'-O—hexadecanoyl-D-maltose, obtained in Example 2 | 5 g |
| Petrolatum oil | 20 g |
| Hydroxyethylcellulose | 0.5 g |
| Imidazolidinyl urea | 0.2 g |
| Water, sufficient amount for | 100 g |

I claim:

1. A process for the preparation of mono $C_7$–$C_{21}$ alkyl or alkenyl esters predominantly in the 6' position of D-maltose, said process comprising, in a first step, forming in an organic solvent a mixed anhydride having the formula (I):

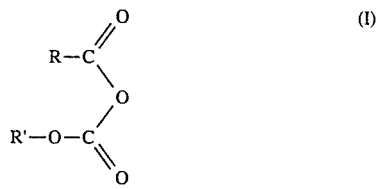

wherein
R represents linear or branched alkyl or alkenyl having 7–21 carbon atoms, or R represents a defined mixture of said alkyl or alkenyl radicals, and
R' represents linear or branched alkyl having from 2 to 10 carbon atoms, by reacting, in the presence of a base, an acid of formula R—COOH wherein R has the meaning given above and an alkyl chloroformate of formula ClCOOR' wherein R' has the meaning given above, and in a second step, reacting the resulting mixed anhydride of formula (I) with D-maltose in solution in an organic solvent selected from the group consisting of pyridine, dimethyl formamide, N-methylpyrrolidone and dimethylacetamide.

2. The process of claim 1 wherein said organic solvent in said first step is selected from the group consisting of tetrahydrofuran, N,N-dimethylformamide and N-methylpyrrolidone.

3. The process of claim 1 wherein said base is selected from the group consisting of triethylamine, pyridine, 4-dimethylaminopyridine, tributylamine and N-methylmorpholine.

4. The process of claim 1 wherein about three equivalents of D-maltose are reacted per equivalent of said acid in said first step.

5. The process of claim 1 which includes subsequent to the reaction in said second step, evaporating said organic solvent and subjecting the resulting product to chromatography on a silica gel column.

6. Monoesters predominantly in the 6' position of D-maltose, obtained by the process of claim 1, and having the formula (II):

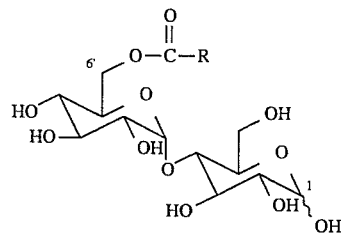

wherein
R represents linear or branched alkyl or alkenyl having 7–21 carbon atoms or R represents a defined mixture of said alkyl or alkenyl radicals, said monoester in position 6' representing about at least 70 percent by weight, the remainder being essentially a monoester in position 1.

7. The monoesters of D-maltose of claim 6 wherein the 6' position monoesters of D-maltose are selected from the group consisting of
6'-O-octanoyl-D-maltose,
6'-hexdecanoyl-D-maltose,
6'-O-oleoyl-D-maltose,
6'-O-dodecanoyl-D-maltose and
6'-O-tetradecanoyl-D-maltose.

8. The process of claim 1 further comprising, after said second step, carrying out a liquid/liquid extraction.

9. The process of claim 8 further comprising, after said second step and before said liquid/liquid extraction, evaporating said organic solvent.

10. A cosmetic composition comprising in a cosmetically suitable vehicle at least one monoester predominantly in the 6' position of D-maltose, said monoester having the formula

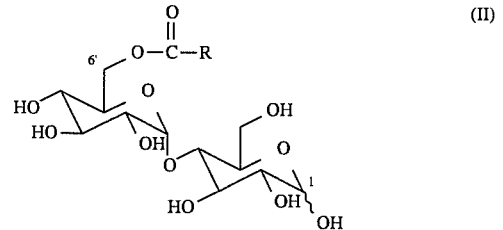

wherein
R represents linear or branched alkyl or alkenyl having 7–21 carbon atoms or R represents a defined mixture of said alkyl or alkenyl radicals, said monoester in position 6' representing about at least 70 percent by weight, the remainder being essentially a monoester in position 1.

11. The composition of claim 10 wherein said monoester of D-maltose is present in an amount ranging from 0.01 to 30 percent by weight based on the total weight of said composition.

12. The composition of claim 10 wherein said monoester of D-maltose is present in an amount ranging from 0.5 to 15 percent by weight based on the total weight of said composition.

13. A buccal-dental composition comprising in a buccodentally acceptable vehicle, at least one mono $C_7$–$C_{21}$ alkyl or alkenyl ester predominantly in the 6' position of D-maltose, said monoester having the formula:

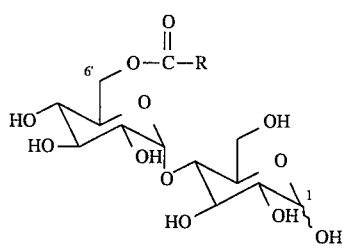

(II)

wherein

R represents linear or branched alkyl or alkenyl having 7–21 carbon atoms or R represents a defined mixture of said alkyl or alkenyl radicals, said monoester in position 6' representing about at least 70 percent by weight, the remainder being essentially a monoester in position 1.

14. A pharmaceutical composition comprising in a pharmaceutically acceptable vehicle at least one mono $C_7$–$C_{21}$ alkyl or alkenyl ester predominantly in the 6' position of D-maltose, said monoester having the formula

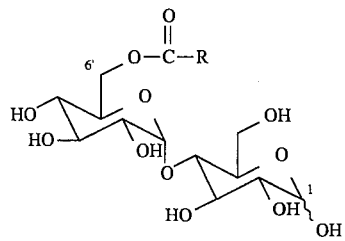

(II)

wherein

R represents linear or branched alkyl or alkenyl having 7–21 carbon atoms or R represents a defined mixture of said alkyl or alkenyl radicals, said monoester in position 6' representing about at least 70 percent by weight, the remainder being essentially a monoester in position 1.

* * * * *